United States Patent [19]
von Angerer et al.

[11] Patent Number: 5,470,854
[45] Date of Patent: Nov. 28, 1995

[54] 2-PHENYLBENZO[B]FURANS, PROCESS FOR THEIR MANUFACTURE AND PHARMACEUTICAL PREPARATIONS CONTAINING THEM

[75] Inventors: Erwin von Angerer, Grasslfing; Sebastian Erber; Martin Schneider, both of Berlin, all of Germany

[73] Assignee: Schering Aktiengesellschaft, Berlin, Germany

[21] Appl. No.: 142,462

[22] PCT Filed: May 25, 1992

[86] PCT No.: PCT/DE92/00435

§ 371 Date: Apr. 14, 1994

§ 102(e) Date: Apr. 14, 1994

[87] PCT Pub. No.: WO92/21669

PCT Pub. Date: Dec. 10, 1992

[30] Foreign Application Priority Data

May 25, 1991 [DE] Germany .................. 41 17 512.3

[51] Int. Cl.⁶ ............... A61K 31/535; C07D 333/64; C07D 307/83
[52] U.S. Cl. ............... 514/233.5; 514/324; 514/443; 514/466; 549/51; 549/466; 546/202; 544/146
[58] Field of Search ............ 549/51, 466; 546/202; 544/146; 514/233.5, 324, 443, 466

[56] References Cited

U.S. PATENT DOCUMENTS

| | | | |
|---|---|---|---|
| 4,133,814 | 1/1979 | Jones et al. | 260/326.55 |
| 4,358,593 | 11/1982 | Jones et al. | 546/202 |
| 4,380,635 | 4/1983 | Peters | 546/202 |
| 4,418,068 | 11/1983 | Jones | 549/51 |
| 4,732,912 | 3/1988 | Pilgrim et al. | 514/510 |
| 4,904,661 | 2/1990 | Pilgrim et al. | 514/237.5 |
| 5,021,414 | 6/1991 | Pilgrim et al. | 514/237.5 |

FOREIGN PATENT DOCUMENTS

| | | |
|---|---|---|
| 0062503 | 10/1982 | European Pat. Off. . |
| 0062505 | 10/1982 | European Pat. Off. . |
| 0062504 | 10/1982 | European Pat. Off. . |
| 0124369 | 11/1984 | European Pat. Off. . |

OTHER PUBLICATIONS

Durani et al., "Structure–Activity Relationship of Antiestrogens: A Study Using Triarylbutenone, Benzofuran, and Triarylfuran Analogues as models for Triarylethylenes and Triarylpropenones", *J. Med. Chem.*, vol. 32 (1989), pp. 1700–1707.

Jones et al., "Antiestrogens. 2. Structure–Activity Studies in a Series of 3–Aroyl–2–arylbenzo[β]thiophene Derivatives Leading to [6-Hydroxy-2-(4-hydroxyphenyl)benzo[β]thien-3-yl][4-[2-(1-piperidinyl)ethoxy]-phenyl] methanone Hydrochloride (LY156758), a Remarkably Effective Estrogen Antagonist with Only Minimal Intrinsic Estrogenicity", *J. Med. Chem.*, vol. 27 (1984), pp. 1057–1066.

Goldenberg et al., "Recherches dans la série des benzofurannes. LLL. Synthèse de dérivés d'hydroxy-5 ou —6 p-hydroxyphényl-2— ou —3 benzofurannes", *Chimica Therapeutica*, vol. 4 (Jul.–Aug. 1973), pp. 398–411.

Naito et al., "Benzofurans as medicinal bactericides and fungicides", *Chemical Abstracts*, vol. 113, No. 5, Abstract No. 34694W (Jul. 30, 1990), p. 48.

Erber et al., "2–Phenylbenzo[b]furans: relationship between structure, estrogen receptor affinity and cytostatic activity against mammary tumor cells", *Chemical Abstracts*, vol. 116, No. 12, Abstract No. 120397V (Mar. 30, 1992), p. 18.

Von Angerer et al., "3–Alkyl-2–phenylbenzo[b]thiophenes: nonsteroidal estrogen antagonists with mammary tumor inhibiting activity", *Chemical Abstracts*, vol. 117, No. 3, Abstract No. 20038F (Jul. 20, 1992), p. 39.

*Primary Examiner*—C. Warren Ivy
*Assistant Examiner*—Amelia Owens
*Attorney, Agent, or Firm*—Millen, White, Zelano & Branigan

[57] ABSTRACT

The invention relates to new furans and thiophenes with the general Formula 1,

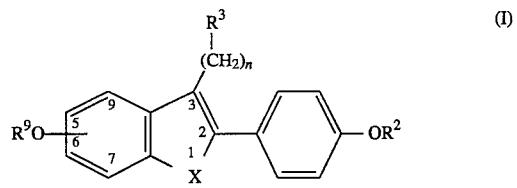

in which $R^1$ and $R^2$ independently of one another denote a hydrogen atom, an alkyl group having 1 to 10 carbon atoms, a benzyl group, a group $C(O)R^4$, where $R^4$ is an alkyl or alkoxy group having 1 to 10 carbon atoms or a phenyl radical, or a carbamoyl group —$C(O)NR^5R^6$, where $R^5$ and $R^6$ independently of one another are a hydrogen atom or an alkyl group having 1 to 10 carbon atoms, and n denotes an integer from 0 to 12 if $R^3$ is a hydrogen atom, or n denotes an integer from 4 to 12 if $R^3$ is an amino group —$NR^7R^8$, where $R^7$ and $R^8$ independently of one another represent a hydrogen atom or an alkyl group having 1 to 10 carbon atoms or $R^7$ and $R^8$ together represent an alkylene group —$(CH_2)_m$— or the group —$(CH_2)_2$— or $R^3$ denotes an amide group —$C(O)NR^7R^8$, where $R^7$ and $R^8$ have the abovementioned meanings, or $R^3$ denotes a sulphinyl group —$S(O)R^3$, where $R^9$ is the radical —$(CH_2)_m(CF_2)_oCF_3$ and m and o are 2, 3, 4, 5 or 6 and x denotes an oxygen or sulphur atom. These new compounds are strong and selective antioestrogens, and have therapeutic applications in the treatment of oestrogen-related illnesses.

10 Claims, No Drawings

2-PHENYLBENZO[B]FURANS, PROCESS FOR THEIR MANUFACTURE AND PHARMACEUTICAL PREPARATIONS CONTAINING THEM

This application is a 371 of PCT/DE92/00435 filed May 25, 1992.

The invention relates to 2-phenylbenzo[b]furans and 2-phenylbenzo[b]thiophens, processes for their manufacture, and pharmaceutical preparations which contain them.

The new furans and thiophenes are characterised by general Formula I

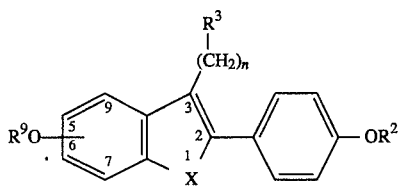

in which $R^1$ and $R^2$ independently of one another denote a hydrogen atom, an alkyl group having 1 to 10 carbon atoms, a benzyl group, a group $C(O)R^4$, where $R^4$ is an alkyl or alkoxy group having 1 to 10 carbon atoms or a phenyl radical, or a carbamoyl group $—C(O)NR^5R^6$, where $R^5$ and $R^6$ independently of one another are a hydrogen atom or an alkyl group having 1 to 10 carbon atoms, and n denotes an integer from 0 to 12 if $R^3$ is a hydrogen atom, or n denotes an integer from 4 to 12 if $R^3$ is an amino group $—NR^7R^8$, where $R^7$ and $R^8$ independently of one another represent a hydrogen atom or an alkyl group having 1 to 10 carbon atoms or $R^7$ and $R^8$ together represent an alkylene group $—(CH_2)_m—$ or the group $—(CH_2)_2O(CH_2)_2—$ or $R^3$ denotes an amide group $—C(O)NR^7R^8$, where $R^7$ and $R^8$ have the abovementioned meanings, or $R^3$ denotes a sulphinyl group $—S(O)R^9$, where $R^9$ is the radical $—(CH_2)_m(CF_2)_oCF_3$ and m and o are 2, 3, 4, 5 or 6 and x denotes an oxygen or sulphur atom.

Radicals of organic carbon acids, which may be saturated or unsaturated, may be considered as alkanoyl groups $—C(O)R^4$. They are derived from aliphatic, cycloaliphatic, aliphatic-cycloaliphatic, cycloaliphatic-aliphatic and aromatic monocarbon acids. The number of carbon atoms in the ring varies from 3 to 7. The alkanoyloxy groups of acetic, propanoic, butyric, isobutyric, pivalic, caproic, acrylic, crotonic, heptylic, caprylic, pelargonic, decanoic, 3-cyclopentylpropanoic and benzoic acids are preferred as radicals $R^1$ and $R^2$.

Radical $R^1$ may be found in positions 4,5,6 and 7 of the bi-cycle, but positions 5 and 6 are particularly well-suited.

Alkyl groups having between 1 and 10 carbon atoms and cycloalkyl groups having between 3 and 7 carbon atoms may be considered as radicals $R^5$ and $R^6$.

Methyl, ethyl, propyl, butyl, pentyl, hexyl, heptyl, octyl, nonyl and decanyl radicals are suitable for alkyl groups $R^5, R^6$, $R^7$ and/or $R^8$. Cyclopentyl and cyclohexyl radicals are mentioned in particular as cycloalkyl groups.

The benzyl group is mentioned in particular as an example of an aralkyl group for radicals $R^4$, $R^5$ and/or $R^6$.

Radicals $R^7$ and $R^8$ may be the same or different or parts of a common ring. If a ring is present, it may contain an oxygen atom in addition to the nitrogen atom. Particularly suitable for these radicals are the following combinations: hydrogen/methyl (derived from methylamine), hydrogen/hydrogen (derived from amine), methyl/methyl (derived from dimethylamine), and the $—(CH_2)_4—$ radical (derived from pyroiidine), the $—(CH_2)_5—$ radical (derived from piperidine), and the $—(CH_2)_2—O—(CH_2)_2$ radical (derived from morpholine).

The invention relates in particular to the following compounds:
5-hydroxy-2-(4-hydroxyphenyl)benzo[b]furan
6-hydroxy-2-(4-hydroxyphenyl)benzo [b]furan
5-hydroxy-2-(4-hydroxyphenyl)-3-methylbenzo [b ]furan
6-hydroxy-2-(4-hydroxyphenyl)-3-methylbenzo[b]furan
3-ethyl-5-hydroxy-2-(4-hydroxyphenyl)benzo[b]furan
3-ethyl-6-hydroxy-2-(4-hydroxyphenyl)benzo[b]furan
5-hydroxy-2-(4-hydroxyphenyl)-3-propylbenzo[b]furan
6-hydroxy-2-(4-hydroxyphenyl)-3-propylbenzo[b]furan
3-butyl-5-hydroxy-2-(4-hydroxyphenyl)benzo[b]furan
3-butyl-6-hydroxy-2-(4-hydroxyphenyl)benzo[b]furan
5-hydroxy-2-(4-hydroxyphenyl)-3-(6-N-piperidylhexyl)-benzo[b]furan
6-hydroxy-2-(4-hydroxyphenyl)-3-(6-N-piperidylhexyl)-benzo[b]furan
6-hydroxy-2-(4-hydroxyphenyl)benzo[b]thiophen
6-hydroxy-2-(4-hydroxyphenyl)-3-methylbenzo[b]thiophen
3-ethyl-6-hydroxy-2-(4-hydroxyphenyl)benzo[b]thiophen
6-hydroxy-2-(4-hydroxyphenyl)-3-propylbenzo[b]thiophen
6-hydroxy-2-(4-hydroxyphenyl)-3-(6-N-piperidinylhexyl-benzo[b]thiophen The invention also relates to a process for manufacturing the 2-phenylbenzo-[b]furans and -thiophens of general Formula I.

According to this process a) if X is finally to be oxygen, a compound of the general formula IIa

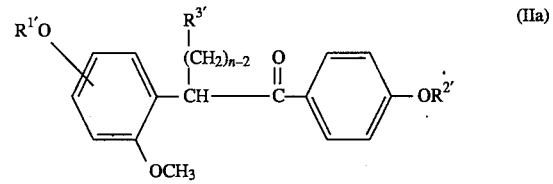

in which
$R^{1'}$ and $R^{2'}$ independently of one another each denote an alkyl group having 1 to 4 carbon atoms and
$R^{3'}$ either denotes $—(CH_2)_2—R$, $—(CH_2)_2—Hal$, where Hal is a halogen atom and in particular a bromine atom, a vinyl radical $—CH=CH_2$ or a radical $—CH_2—C(O)NR^7R^8$ is cyclised with a Lewis acid with cleavage of the ether groups to give a compound of the general formula Ia

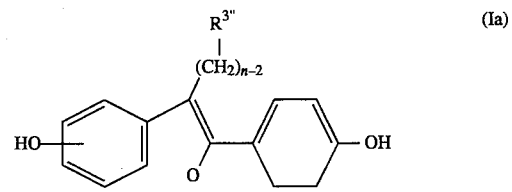

and if $R^{3'}$ denotes $—(CH_2)_2—Hal$, Hal is exchanged by reaction of the compound of the formula Ia with a primary, secondary or cyclic amine of the formula $HNR^7R^8$ for the corresponding amine radical $—NR^7R^8$ or by reaction with a fluoroalkylthiol of the formula $H—S—R^9$ for the corresponding thiofluoroalkyl radical $—S—R^9$ and the latter is oxidised with hydrogen peroxide or another oxidising agent to give the sulphoxide $—S(O)—R^9$ or, if $R^{3'}$ denotes a vinyl radical, by terminal hydroxylation of the vinylic double bond, conversion of the resulting hydroxyl group to a better leaving group and this, analogously to the case in which $R^{3'}$ denotes a halogen atom, is exchanged for an amine radical —$NR^7R^8$ or thiofluoroalkyl radical —S—$R^9$ and the latter is oxidised to the sulphoxide $S(O)R^9$ or if $R^{3'}$ denotes the radical —$CH_2$—$C(O)NR^7R^8$, this is retained as $R^3$ or the carbonyl group is completely reduced with lithium aluminium hydride and the free hydroxy groups are optionally etherified or esterified, or b) if X is finally to be sulphur, a compound of the general formula IIb

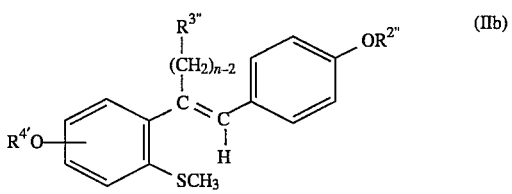

in which $R^{1'}$ and $R^{2'}$ have the same meaning as in formula IIa and $R^{3''}$ denotes —$(CH_2)_2$—R, —$(CH_2)_2$—Hal, where Hal is a halogen atom and in particular a bromine atom, or a vinyl radical —$CH=CH_2$, is cyclised with a mixture of sulphuryl chloride and pyridine to give the corresponding benzo[b]thiophene derivative of the general formula Ib

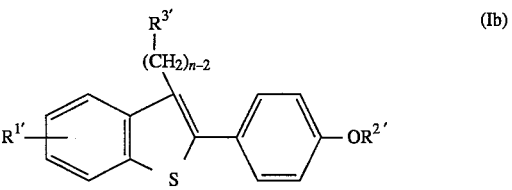

and then if $R^{3''}$ denotes —$(CH_2)_2$—Hal or a vinyl radical —$CH=CH_2$ the compound of the general formula Ib is further reacted as indicated for these two cases in a) and then the ether groups are optionally cleaved with a Lewis acid and the free hydroxy groups are optionally etherified or esterified, or c) if X is finally to be sulphur, a compound of the general formula IIc

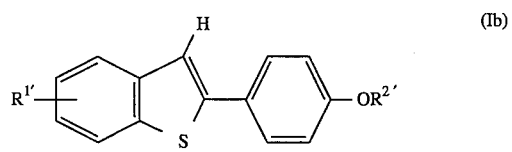

in which $R^{1'}$ and $R^{2'}$ have the same meaning as in formula IIa, is acylated with an acid halide of the general formula $R^{3'}$—$(CH_2)_{n-3}$—$C(O)X$, where $R^{3'}$ and n have the same meaning as in Formula IIa and X is a chlorine or bromine atom, and subsequently reduced with $LiAlH_4/AlCl_3$ to give a compound of the general formula Ic

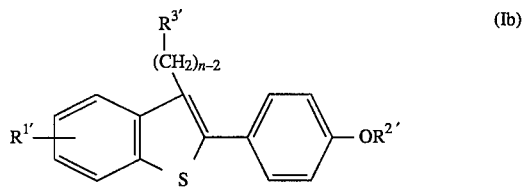

and the latter is further reacted as described in a).

The ethyl, propyl-isopropyl, butyl, isobutyl, tert, butyl and particularly the methyl groups can be considered as possible $R^{1'}$ and $R^{2'}$ alkyl groups.

The cyclization of the compounds of general formula IIa into compounds of general formula Ia with a Lewis acid proceeds under (simultaneous) separation of the ether groupings $R^{1'}$—O— and $R^{2'}$—O— and formation of the corresponding free hydroxy compounds.

Suitable reagents for the cyclization and ether separation are boron tribromide, boron trifluoride, aluminium trichloride, silicon tetrachloride, aluminium tribromide, sodium methylthiolate and trimethylsilyliodide. The reaction is carried out at temperatures of between −70° and 200° C. Inert solvents may be considered as possible solvents for this cyclization and ether separation. These include aliphatic halogenated hydrocarbons, e.g. methylene chloride, or aromatic hydrocarbons such as chlorobenzene, dichlorobenzene and dimethylformamide, as well as acetonitrile. Aliphatic ethers with alkyl radicals of 1–6 carbon atoms are, however, also suitable.

The processes used in esterification of the phenolic hydroxyl groups are the normal esterification processes used in chemistry. Examples include reaction with a carbon acid, or a carbon acid anhydride in the presence of strong acids, e.g. trifluoroacetic acid, perchloric acid or p-toluolsulphonic acid at room temperature or slightly above it, or reaction with a carbon acid anhydride in the presence of a tertiary amine at around 20°–80° C.

If pyridine and 4-dimethylaminopyridine are used together as tertiary amines, esterification is preferably carried out at room temperature. The remaining steps in the production of the benzo[b]furans of general Formula I (X=0) included in this invention are carried out according to standard methods used in organic chemistry. Coupling of the basic fragment —$NR^7R^8$ to the compounds of general Formula Ia, where R3' signifies —$(CH_2)_2$Hal, results from boiling the ω-halogen compound in the corresponding amine.

The selective hydroxylisation of the vinyl double bond, i.e. if $R^{3'}$ is —$CH=CH_2$, is obtained by hydroboration, for example with 9-borobicyclo [3.3.1] nonane. The ω-hydroxy compound thus formed is then converted by treatment with methanesulphonyl chloride and triethylamine into the corresponding mesylate. The hydroxy group can of course be replaced by other suitable leaving groups, e.g. a bromine atom, the tosyl radical, the trifluoromethanesulphonate group or similar leaving groups. Coupling of the basic fragment is obtained as described above, the temperature varying according to the reactivity of the leaving group.

To produce benzo[b]thiophens of general Formula I(X=S) an orthothiomethylstyrol of general Formula IIb is cyclized with a mixture of sulphuryl chloride and pyridine. The orthothiomethylstyrol reacts to form the corresponding sulphonium chloride, which is converted with pyridine into the corresponding chlorosulphide through separation of methylchloride, and subsequently cyclises through losing HCl into the corresponding benzo[b]thiophen. Any subsequently neccessary conversion is carried out as described in the case of the benzo[b]furans.

Alternatively, it is possible to start with the unsubstituted heterocyclus in position 3, and to introduce the side chain through Friedl and Craft's acylation and a subsequent reduction with $LiAlH_4/AlCl_3$.

The compounds of general Formula I which comprise the invention have been found to possess strong anti-oestrogenic properties.

Compounds with anti-oestrogenic properties, i.e. substances with inhibiting effects on oestrogen, have been described in the literature.

For example, Tamoxifen can be cited as an anti-oestrogen (Eur. J. Cancer Clin. Oncol., 1985, 21, 985 and J. S. Patterson "10 Years of Tamoxifen in Breast Cancer" in Hormonal Manipulation of Cancer; Peptides, Growth Factors and New (Anti) Steroidal Agents. Raven Press, New York, (1987)).

Steroidal anti-oestrogens are described in European Patent Application 0 138 504. Anti-oestrogen Indole derivatives are found in German letters patent 32 32 968, in J. Med. Chem. 1983, 26, 113; J. Med. Chem., 1984, 27, 1439, Eur. J. Cancer. Clin. Oncol. 1985, 21, 531 Cancer Treatment Reviews 1984, 11, 147, while N-aminoalkylindoles. which, along with pronounced anti-oestrogen effectiveness, display only slight oestrogen activity, are to be found in European Patent Application 0 348 341.

Hydroxylised 2-phenylindoles, existing in the form of diamineplatinum (II)-complex-compounds, are mentioned in German Published Application (Offenlegungsschrift) 37 30 746.

The compounds of general Formula I which comprise the invention possess a marked affinity to the estradiol receptor, and displace competitively $^3H$-17β-Estradiol from the receptor. In vivo, they possess strong anti-oestrogenic effects in the uterus of the mouse, and inhibit oestrogen-stimulating uterus growth up to 100%. In these tests, oestrogenic effects cannot be detected, or only to a very small degree. The compounds have an inhibiting effect on the growth of hormone-dependent tumor cells, and inhibit in particular the growth of oestrogen-dependent mammarial tumour cells in humans. (MCF-7).

The compounds which comprise the invention have applications in the therapeutic treatment of oestrogen-dependent illnesses such as prostate hyperplasia, mammarial carcinoma, endometrial carcinoma, anovulatory infertility and melanoma.

The following pharmacological tests show the effectiveness of the compounds which comprise the invention.

Table I gives an overall view of the compounds of general Formula I which were tested, and their relative bonding affinities (RBA*) to the oestrogen receptor of a calf's uterus, in relation to 17β-estradiol=100.

The test methodology is described in Cancer Treatment Reviews 1984, 11, 147.

Table 1 shows that compounds 104a, 104b, 102a, 106b, 106a, 63a and 62a display the greatest affinity in relation to estradiol.

Table 2 shows the oestrogenic and anti-oestrogenic effectiveness of compounds 62a, 62b, 68a, 68b, 102a, 104a, 104b, 106a, and 106b. The effectiveness of these compounds was found in an in-vivo test on infantile mice. This test is extensively described in Cancer Treatment Reviews 1984, 11, 147, and J. Med. Chem., 1984, 27, 1439.

Table 3 shows the results of examinations of the cystostatic activity of compounds 61a, 62a, 63a, 68a and of 102a, 104a, 106a, 102b, 104b, 106b, 119b in relation to Tamoxifen. A strongly inhibiting effect on the growth of hormone-sensitive human MCF-7 mamma carcinoma cells was found.

TABLE 1

Tests on Formula 1 compounds and their relative bonding affinities to the oestrogen receptor $$\text{HO} \begin{array}{c} 5 \\ 6 \end{array} \begin{array}{c} 9 \\ 7 \end{array} \begin{array}{c} 3 \\ 2 \\ 1 \end{array} \begin{array}{c} (CH_2)_n \\ R^3 \end{array} \text{—OH} \quad (I)$$

| Compound | X | n | $R^3$ | 5 or 6-OH | RBA* |
|---|---|---|---|---|---|
| 61a | O | 1 | H | 5 | 2,0 |
| 61b | O | 1 | H | 6 | 0,2 |
| 62a | O | 2 | H | 5 | 15,7 |
| 62b | O | 2 | H | 6 | 0,6 |
| 63a | O | 3 | H | 5 | 20,0 |
| 63b | O | 3 | H | 6 | 1,7 |
| 64a | O | 4 | H | 5 | 1,6 |
| 64b | O | 4 | H | 6 | 0,6 |
| 68a | O | 6 | N-Piperidyl- | 5 | 4,3 |
| 68b | O | 6 | N-Piperidyl | 6 | 5,4 |
| 102a | S | 1 | H | 5 | 26,0 |
| 102b | S | 1 | H | 6 | 9,7 |
| 104a | S | 2 | H | 5 | 59,6 |
| 104b | S | 2 | H | 6 | 27,6 |
| 106a | S | 3 | H | 5 | 21,9 |
| 106b | S | 3 | H | 6 | 25,1 |
| 119b | S | 6 | N-Piperidyl | 6 | 7,1 |

*Relative bonding affinities to the oestrogen receptor of calves' uteri, in relation to 17β-estradiol = 100

TABLE 2

Uterotrophic and anti-uteroptrophic effects on infantile mice

| compound | uterotrophic test | | anti-uterotrophic test | | |
|---|---|---|---|---|---|
| | dosage, μg[a] | effect[b] | dosage [a,c] | effect[b] | inhibition, % |
| control | — | 15.5 ± 2.9 | — | 13.1 ± 2.1 | |
| oestrone | 0.4 | 53.4 ± 3.6 | 0.4 | 42.0 ± 6.2 | |
| 62a | 1 | 10.5 ± 1.9 | 1 | 44.2 ± 7.8 | — |
| | 5 | 14.6 ± 2.4 | 5 | 39.1 ± 4.2 | 10 |
| | 25 | 19.0 ± 4.4 | 25 | 35.6 ± 2.6 | 22 |
| control | — | 14.7 ± 3.4 | — | 14.7 ± 3.4 | |
| oestrone | 0.4 | 54.6 ± 6.1 | 0.4 | 54.6 ± 6.1 | |
| 62b | 1 | 12.9 ± 2.5 | | | |
| | 5 | 14.5 ± 3.7 | 5 | 60.3 ± 5.8 | — |
| | 25 | 17.0 ± 3.3 | 25 | 56.9 ± 7.1 | — |
| | 125 | 18.3 ± 6.3 | 125 | 49.8 ± 7.9 | 12 |

TABLE 2-continued

| | | | | | |
|---|---|---|---|---|---|
| control | — | 14.6 ± 3.7 | — | 14.6 ± 3.7 | |
| oestrone | 0.4 | 67.0 ± 9.0 | 0.4 | 67.0 ± 9.0 | |
| 68a | 1 | 16.1 ± 2.1 | | | |
| | 5 | 17.3 ± 2.9 | 5 | 38.1 ± 7.5 | 55 |
| | 25 | 15.8 ± 1.9 | 25 | 37.6 ± 6.2 | 56 |
| | 125 | 17.3 ± 3.2 | 125 | 41.8 ± 6.4 | 48 |
| control | — | 14.1 ± 1.6 | — | 14.1 ± 1.6 | |
| oestrone | 0.4 | 63.5 ± 5.7 | 0.4 | 63.5 ± 5.7 | |
| 68b | 1 | 18.3 ± 1.9 | | | |
| | 5 | 18.8 ± 3.0 | 5 | 58.6 ± 7.1 | 10 |
| | 25 | 24.4 ± 3.8 | 25 | 59.9 ± 6.6 | 7 |
| | 125 | 21.4 ± 3.7 | 125 | 68.7 ± 9.9 | |

| | uterotrophic test | | anti-uterotrophic test | | |
|---|---|---|---|---|---|
| Verb. | dosage, μg[a] | effect[b] | dosage [a,c] | effect[b] | inhibition, % |
| control | — | 12.4 ± 1.6 | — | 12.4 ± 1.6 | |
| oestrone | 0.4 | 46.3 ± 1.4 | 0.4 | 46.3 ± 1.4 | |
| 102a | 1 | 15.8 ± 2.1 | | | |
| | 5 | 20.8 ± 2.7 | 5 | 42.4 ± 4.0 | 12 |
| | 25 | 15.7 ± 2.3 | 25 | 23.1 ± 3.8 | 68 |
| | 125 | 18.5 ± 3.0 | 125 | 32.2 ± 3.8 | 42 |
| 104a | 0.2 | 27.6 ± 3.8 | 0.2 | 49.8 ± 1.4 | — |
| | 1 | 30.3 ± 7.7 | 1 | 35.3 ± 7.3 | 32 |
| | 5 | 38.5 ± 5.4 | 5 | 37.0 ± 3.4 | 27 |
| | 25 | 44.2 ± 6.6 | 25 | 44.1 ± 6.7 | — |
| | 125 | 19.6 ± 5.2 | 125 | 36.3 ± 4.0 | 30 |
| control | — | 16.5 ± 3.3 | — | 16.5 ± 3.3 | |
| oestrone | 0.4 | 41.0 ± 6.6 | 0.4 | 41.0 ± 6.6 | |
| 106a | 1 | 25.4 ± 6.2 | | | |
| | 5 | 32.7 ± 5.0 | 5 | 34.4 ± 7.1 | 27 |
| | 25 | 35.3 ± 7.5 | 25 | 48.0 ± 4.2 | — |
| | 125 | 51.2 ± 9.9 | 125 | 48.8 ± 4.1 | — |
| control | — | 12.6 ± 2.0 | — | 12.6 ± 2.0 | |
| oestrone | 0.4 | 49.6 ± 7.4 | 0.4 | 49.6 ± 7.4 | |
| 102b | 1 | 10.9 ± 2.1 | | | |
| | 5 | 12.1 ± 1.9 | 5 | 47.0 ± 7.8 | 7 |
| | 25 | 16.9 ± 2.9 | 25 | 38.5 ± 3.7 | 30 |
| | 125 | 21.9 ± 4.6 | 125 | 38.1 ± 5.8 | 31 |
| 104b | 1 | 18.0 ± 4.0 | | | |
| | 5 | 22.7 ± 5.9 | 5 | 37.9 ± 6.9 | 32 |
| | 25 | 29.3 ± 4.5 | 25 | 37.3 ± 4.2 | 33 |
| | 125 | 39.9 ± 6.1 | 125 | 38.0 ± 5.4 | 31 |

| | uterotrophic test | | anti-uterotrophic test | | |
|---|---|---|---|---|---|
| compound | dosage, μg[a] | effect[b] | dosage [a,c] | effect[b] | inhibition, % |
| 106b | 1 | 16.6 ± 4.6 | | | |
| | 5 | 22.4 ± 3.1 | 5 | 37.0 ± 6.5 | 34 |
| | 25 | 24.5 ± 4.8 | 25 | 35.3 ± 6.7 | 39 |
| | 125 | 35.1 ± 4.9 | 125 | 34.8 ± 6.2 | 40 |
| control | — | 17.7 ± 3.0 | — | 17.7 ± 3.0 | |
| oestrone | 0.4 | 49.0 ± 6.4 | 0.4 | 49.0 ± 6.4 | |
| 119b | 1 | 19.8 ± 3.1 | | | |
| | 5 | 20.7 ± 5.0 | 5 | 26.1 ± 5.4 | 73 |
| | 25 | 19.4 ± 2.1 | 25 | 22.8 ± 2.6 | 65 |
| | 125 | 34.2 ± 9.5 | 125 | 30.0 ± 5.6 | 61 |

[a]dosage/animal, administered s.c. on three consecutive days in olive oil solution.
[b]uterus dry weight (mg)/body weight (g) × 100, determined 24 hours after the final injection.
[c]simultaneous administration of 0.4 μg oestron/animal/day.

TABLE 3

Effect of 2-phenylbenzo[b]furans and -thiophens on cell growth of MCF-7 cells. Data given as corrected T/C values (%).

| | T/C[a] [%] | | | |
|---|---|---|---|---|
| compound | $1 \times 10^{-7}$ M[b] | $1 \times 10^{-6}$ M[b] | $5 \times 10^{-6}$ M[b] | $1 \times 10^{-5}$ M[b] |
| Tam | 56.5 ± 16.3[c] | 59.1 ± 14.1[c] | 33.6 ± 10.3[c] | −5.7 ± 3.4[c] |
| 61a | 72.3 ± 18.2 | 78.1 ± 17.2 | 37.7 ± 11.9[c] | 13.3 ± 5.3[c] |
| 62a | 65.0 ± 13.5[c] | 49.0 ± 12.6[c] | 0.3 ± 3.8[c] | −0.2 ± 2.9[c] |
| 63a | 51.0 ± 11.3[c] | 50.5 ± 8.8[c] | −0.1 ± 3.6[c] | −2.1 ± 2.8[c] |

TABLE 3-continued

Effect of 2-phenylbenzo[b]furans and -thiophens on cell growth of MCF-7 cells. Data given as corrected T/C values (%).

| compound | T/C[a] [%] | | | |
|---|---|---|---|---|
|  | $1 \times 10^{-7}$ M[b] | $1 \times 10^{-6}$ M[b] | $5 \times 10^{-6}$ M[b] | $1 \times 10^{-5}$ M[b] |
| 68a | 64.4 ± 12.0[c] | 51.6 ± 10.2[c] | 10.4 ± 4.8[c] | −9.9 ± 1.8[c] |
| 68b | 58.7 ± 17.1[c] | 42.9 ± 7.7[c] | 12.1 ± 5.4[c] | −9.6 ± 2.9[c] |
| Tam | 56.5 ± 16.3[c] | 59.1 ± 14.1[c] | 33.6 ± 10.3[c] | −5.7 ± 3.4[c] |
| 102a | 71.3 ± 18.8 | 87.4 ± 20.0 | 48.5 ± 14.7[c] | 14.7 ± 6.4[c] |
| 104a | 61.2 ± 22.1[c] | 59.1 ± 15.9[c] | 2.4 ± 3.9[c] | 3.2 ± 3.2[c] |
| 106a | 77.1 ± 21.4 | 35.0 ± 10.4[c] | 2.3 ± 4.1[c] | 0.3 ± 3.5[c] |
| 102b | 124.6 ± 37.2 | 133.3 ± 43.4 | 54.9 ± 17.9[c] | 10.9 ± 6.7[c] |
| 104b | 94.0 ± 21.2 | 91.9 ± 21.2 | 5.7 ± 5.8[c] | 4.2 ± 6.0[c] |
| 106b | 81.7 ± 17.5 | 69.0 ± 15.1[c] | 3.6 ± 3.0[c] | 1.8 ± 3.1[c] |
| 119b | 18.8 ± 7.2[c] | 48.1 ± 12.4[c] | 2.0 ± 3.6[c] | −13.5 ± 3.2[c] |

[a]Inhibiting effect on MCF-7 cells: quotient of optical densities from Test-(T) and control group (C); mean value of 16 individual results; standard deviation through error reckoning according to GAUSS.
[b]Substance concentration (mol/l) in incubation medium.
[c]Significant $p < 0.01$ in relation to control group (C).

The invention also relates to pharmaceutical preparations which contain at least one of the general Formula I compounds, and the use of these compounds for the treatment of oestrogen-dependent illnesses and tumours.

The compounds which comprise the invention can be used in the manufacture of pharmaceutical compositions and preparations. The pharmaceutical compositions or medicaments contain as an effective ingredient one or more of the compounds which comprise the invention, and as necessary may be combined with other pharmacological or pharmaceutical substances. The medicaments are manufactured according to known methods, according to which known and customary pharmaceutical process materials or other customary carriers and diluents may be used.

The type of carriers and process materials which may, for example, be used are such as are recommended or described in the following sources as process materials for pharmacology, cosmetics and related fields: Ullman's Encyclopaedia of Technical Chemistry, Vol. 4 (1953), pp 1–39; Journal of Pharmaceutical Sciences, Vol. 52 (1963), pp 918 onwards; H. v. Czetsch-Lindenwald, Process Materials for Pharmacology and Related Fields: Pharm. Ind. Book 2., 1961, p 72 onwards; Dr. H. P. Fielder, Lexicon of Process Materials for Pharmacology, Cosmetics and Related Fields, Cantor K. G. Aulendorf in Wurttemburg 1971.

Administration of the compounds may be oral, parenteral, intraperitoneal, intramuscular, subcutaneous or percutaneous. The compounds may also be implanted in tissue. The amount of the compound to be administered varies within a wide range, and may include any effective quantity. Depending on the condition treated and the method of administration, the amount of compound administered may be 0.01–100 mg/kg bodyweight, or preferably 0.1–20 mg/kg bodyweight per day.

Oral administration may be by means of capsules, pills, tablets, dragées, etc. The dosage may contain, along with the active ingredient, a pharmaceutically tolerable carrier, for example starch, sugar, sorbitol, gelatine, slip additive, silicic acid, talc etc. The individual dosage units for oral application may for example contain 10 to 100 mg of the active ingredient.

In the case of parenteral administration, the active ingredients may be dissolved or suspended in a physiologically tolerable diluent. Very frequently, oils are used as diluents, with or without the addition of a solubilizer, a surface-active agent, or a suspending or emulsifying agent. Examples of oils which may be used are olive oil, groundnut oil, cotton seed oil, soya bean oil, castor oil and sesame oil.

The compounds can also be used in the form of a depot injection or implant preparation, formulated in such a way as to permit delayed release of the active ingredient.

Implants may contain such inert materials as biologically degradable polymers, or synthetic silicons such as silicon rubber. In addition, the active ingredients may for example be incorporated into a sticking plaster for percutaneous application.

In the following procedural instructions and examples, the invention is explained in greater detail.

The reaction diagrams for manufacturing the compounds comprising the invention and the neccessary intermediate products are shown in illustrations 1 to 4.

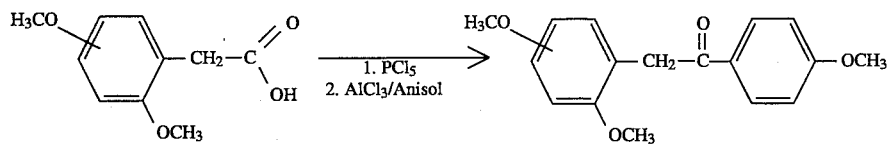

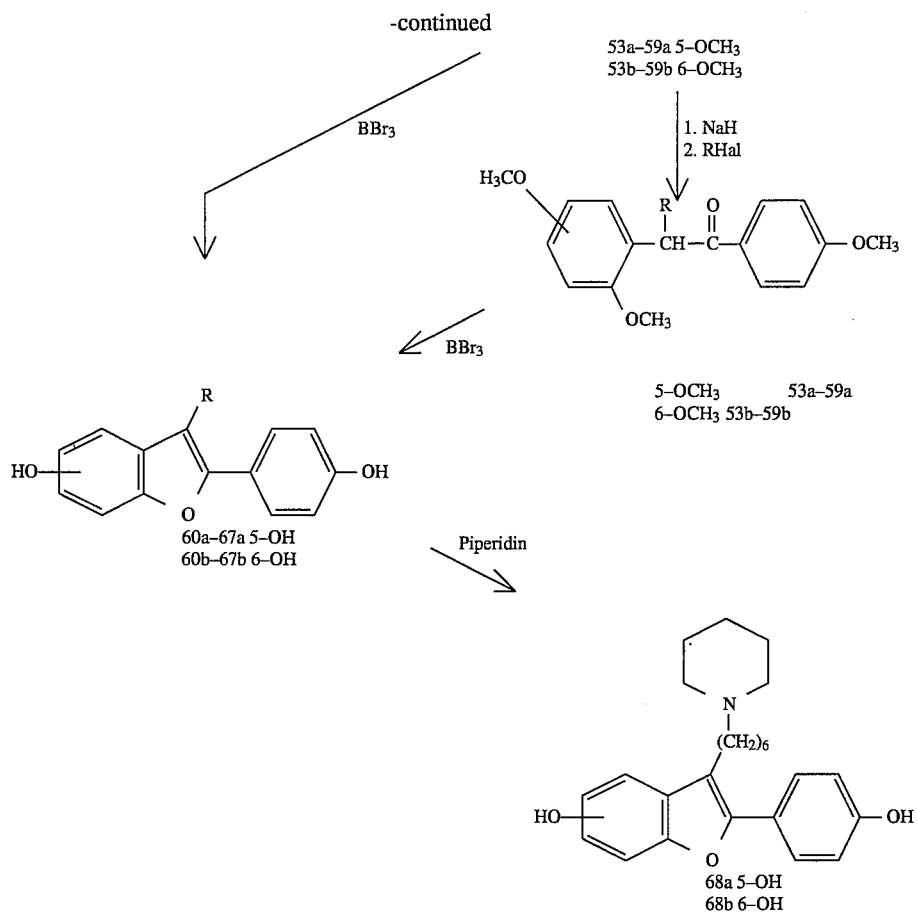
Ill. 1: Synthesis plan for the preparation of 2-Phenylbenzo[b]furans
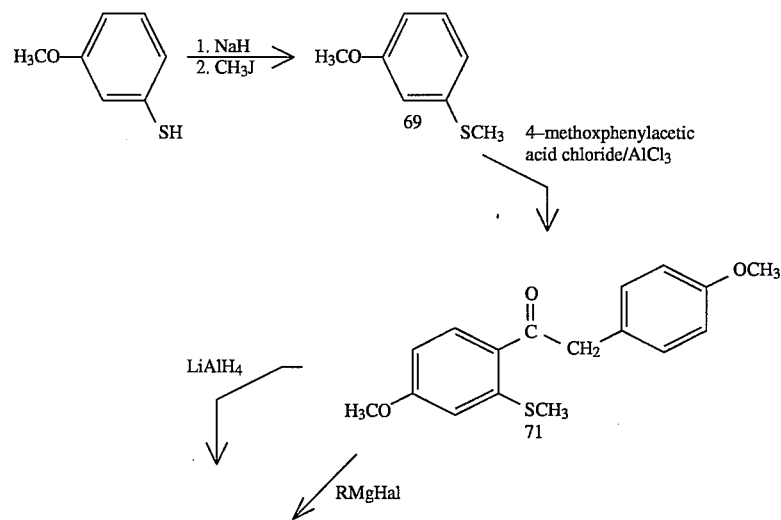

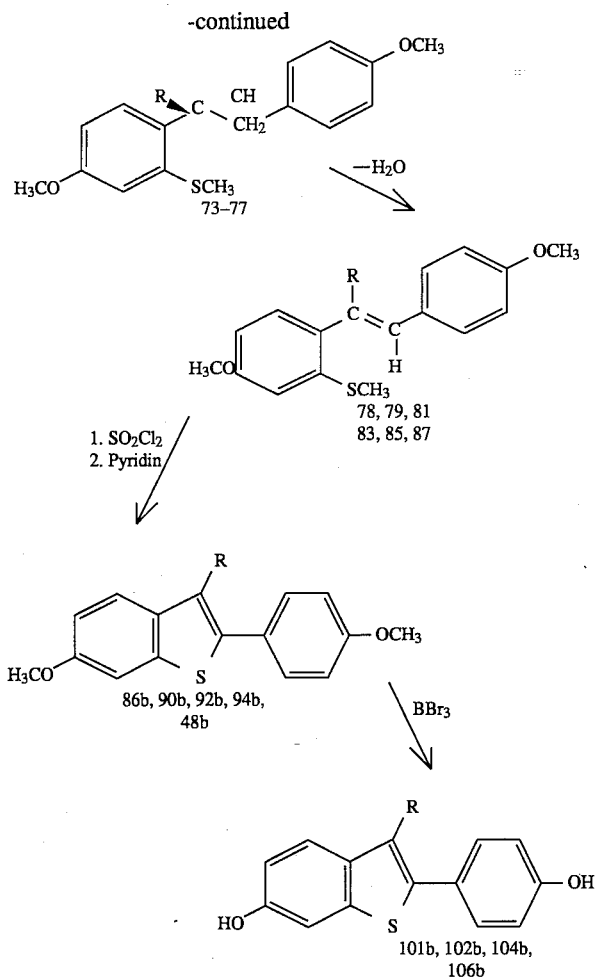
Ill. 2: Synthesis plan for preparation of 6-hydroxy-2-phenylbenzo[b]thiophens.
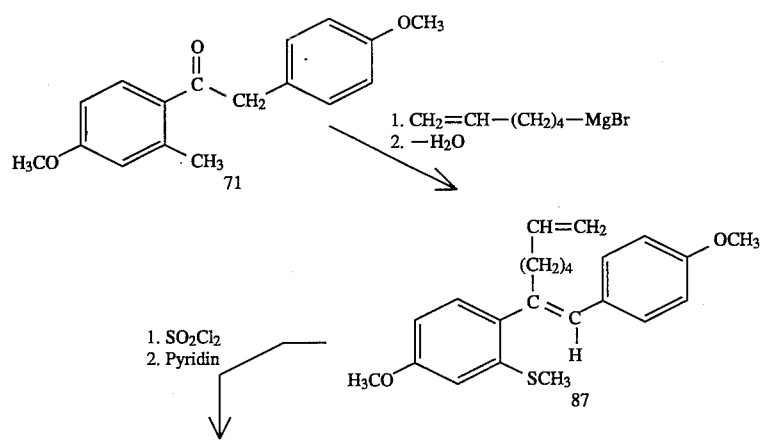

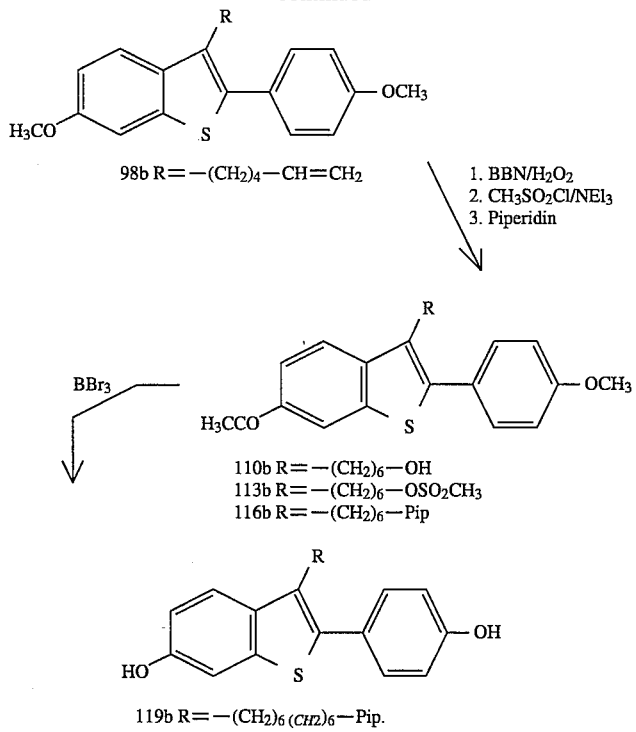
Ill. 3: Synthesis plan for the preparation of 6-hydroxybenzo[b]thiophens with structural fragments.
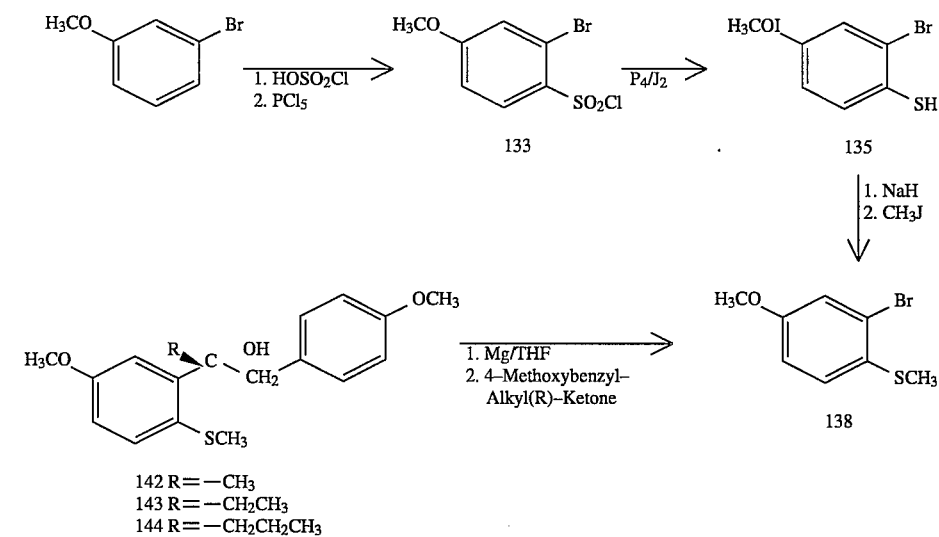

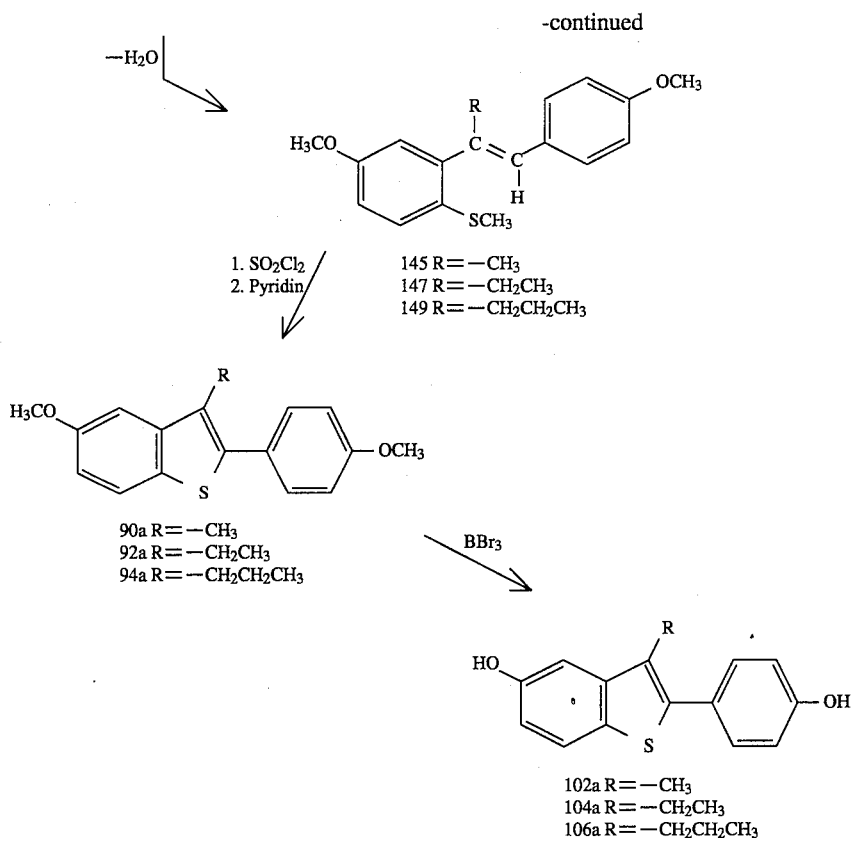

Ill. 4: Synthesis plan for the preparation of 5-hydroxy-2-Phenylbenzo[b]thiophens.

2,4-dimethoxyphenylacetic acid (48)

In a 250 ml round-bottomed flask with a reflux condenser, 20.0 g (0.11 mol) 2,4-dimethoxyacetophenon, 19.32 g (0.22 mol) morpholine (19.3 ml) and 7.12 g (0.22 mol) sulphur are heated for ca. 20 hours at 135° C. Following this, any remaining morpholine is removed in a vacuum. The remaining thiomorpholide is saponified without further purification.

Saponification: The brown oil is mixed with 90 g 50% KOH in 160 ml of ethanol and refluxed for 6 hours. Following this a large part of the alcohol is distilled off, it is diluted with water and solid constituents filtered out. It is then ice-cooled, acidified with concentrated hydrochloric acid, extracted three times with dichloromethane, dried over MgSO4, filtered and concentrated in a water jet vacuum. The raw product is recrystallised from water.

beige crystals: M.P.: 106°–108° C.; yield: 51%

Preparation of acid chloride

A mixture of 0.5 mol carbonic acid and 0.5 mol phosphorpentachloride is ice-cooled and stirred for half an hour. Following this it is warmed to 60°, and the phosphorylchloride which is produced is drawn off in a vacuum. The residue is added to absolute benzol and condensed again, in order to remove remaining phosphoryl chloride. The residue is converted without further purification.

2,5-dimethoxyphenylacetic acid chloride (50a)
  colourless oil: yield: 97% IR(Film): 1805 cm$^{-1}$ (s;C=O)
2,4-dimethoxyphenylacetic acid chloride (50b)
  yellow oil: yield: 97% IR(Film): 1810 cm$^{-1}$ (s;C=O)

Friedel-Craft's acylation

A solution of 0.05 mol carbonic acid in 150 ml 1,2-dichloroethane is added to 10.8 g (0.1 mol) anisole. It is ice-cooled and stirred, and 13.3 g (0.1 mol) aluminium trichloride added in portions. It is kept stirring overnight at room temperature, and then ca. 200 ml of iced water are poured on. After separation of the organic phase the aqueous phase is extracted three times with dichloromethane. The combined organic phases are washed twice with 10% sodium hydroxide solution and three times with water, dried over MgSO4, filtered and condensed in a vacuum. The residue is purified by column chromatography (silica gel 60; dichloromethane) and recrystallised from ethanol.

2-(2,5-dimethoxyphenyl)-1-(4-methoxypenyl)ethanon (51a)
  Educt: 2,5-dimethoxyphenylacetic acid chloride (50a) anisole
  colourless crystals: M.P.: 105°–107° C. yield: 76%
2-(2,4-dimethoxyphenyl)-1-(4-methoxyphenyl)ethanon (51b)
  Educt: 2,4-dimethoxyphenylacetic acid chloride (50b) anisole
  colourless crystals: M.P.: 100°–102° C. yield: 48%

Preparation of 2-alkyl-1,2-diarylethanons 0.5 g (21.0 mol) sodium hydride (80% in paraffin) are ice-cooled and stirred for 15 minutes at 0° C. in suspension in 80 ml absolute dimethylformamide (DMF). This is followed by dropwise addition of a solution of 4.0 g (14.0 mmol) 1,2-diarylethanon in 40 ml absolute DMF. which is stirred (ca. 30 minutes) until gas no longer develops. A solution of 21.0 mmol alkylhalogenide in 20 ml absolute DML is added dropwise to the cooled mixture. It is stirred for half an hour at 0° C., taken out of the cooling bath, and stirred for half an hour at room temperature. Surplus sodium hydride is disposed of by pouring into iced water. The hydrolysate is extracted three times with ether, washed twice with water, dried over MgSO4, filtered and condensed in a water jet vacuum. The residue is chromatographed with dichloromethane over silica gel 60. Crystalline products are recrystallised from ethanol.

2-(2,5-dimethoxyphenyl)-1-(4-methoxyphenyl)propanon (53a)

Educt: 2-(2,5-dimethoxyphenyl)-1-(4-methoxyphenyl)ethanon (51a) methyl iodide colourless crystals: M.P.: 97°–98° C. yield: 71%

2-(2,4-dimethoxyphenyl)-1-(4-methoxyphenyl)propanon (53b)

Educt: 2-(2,4-dimethoxyphenyl)-1-(4-methoxyphenyl)ethanon (51b) methyl iodide colourless crystals: M.P.: 59°–60° C. yield: 38%

2-(2,5-dimethoxyphenyl)-1-(4-methoxyphenyl)butanon (54a)

Educt: 2-(2,5-dimethoxyphenyl)-1-(4-methoxyphenyl)ethanon (51a) ethyl iodide yellow oil: yield: 67% IR(Film): 1680 $cm^{-1}$ (s:C=O)

2-(2,4-dimethoxyphenyl)-1-(4-methoxyphenyl)butanon (54b)

Educt: 2-(2,4-dimethoxyphenyl)-1-(4-methoxyphenyl)ethanon (51b) ethyl iodide yellow oil: yield: 69% IR(Film): 1680 $cm^{-1}$ (s:C=O)

2-(2,5-dimethoxyphenyl)-1-(4-methoxyphenyl)propanon (55a)

Educt: 2-(2,5-dimethoxyphenyl)-1-(4-methoxyphenyl)ethanon (51a) propyl iodide yellow oil: yield: 81% IR(Film): 1680 $cm^{-1}$ (s:C=O)

2-(2,4-dimethoxyphenyl)-1-(4-methoxyphenyl)pentanon (55b)

Educt: 2-(2,4-dimethoxyphenyl)-1-(4-methoxyphenyl)ethanon (51b) propylyl iodide yellow oil: yield: 72% IR(Film): 1680 $cm^{-1}$ (s:C=O)

2-(2,5-dimethoxyphenyl)-1-(4-methoxyphenyl)hexanon (56a)

Educt: 2-(2,5-dimethoxyphenyl)-1-(4-methoxyphenyl)ethanon (51a) butyl iodide colourless crystals: M.P.: 62°–63° C. yield: 83%

2-(2,4-dimethoxyphenyl)-1-(4-methoxyphenyl)hexanon (56b)

Educt: 2-(2,4-dimethoxyphenyl)-1-(4-methoxyphenyl)ethanon (51b) butyl iodide yellow oil: yield: 77% IR(Film): 1680 $cm^{-1}$ (s:C=O)

8-bromine-2-(2,5-dimethoxyphenyl)-1-(4-methoxyphenyl)octanon (59a)

In this case the cooled mixture of 1,2 diarylethanon and sodium hydride is added dropwise to the 1,6-dibrominehexane solution. 2-(2,5-dimethoxyphenyl)-1-(4-methoxyphenyl)ethanon (51a) and 1,6-dibrominehexane were used as educts.

yellow oil: yield: 61% IR(Film: 1675 cm$^{-1}$ (s;C=O)

8-bromine-2-(2,4-dimethoxyphenyl)-1-(4-methoxyphenyl)octanon (59b)

In this case the cooled mixture of 1,2diarylethanon and sodium hydride is added dropwise to the 1,6-dibrominehexane solution. 2-(2,4-dimethoxyphenyl)-1-(4-methoxyphenyl)ethanon (51b) and 1,6-dibrominehexane were used as educts.

yellow oil: yield: 48% IR(Film): 1675 $cm^{-1}$ (s:C=O)

Methylation of thiophenols 5.3 g (0.22 mol) sodium hydride is suspended in 100 ml absolute dimethylformamide (DMF), and stirred for 30 minutes in the ice bath. At 0° C. 0.15 mol of the thiophenol is slowly added dropwise to 50 ml absolute DMF. The mixture is stirred until gas is no longer noticeably given off. Following this, a solution of 22.7 g (0.16 mol; 2.44 ml) methyl iodide is added dropwise to 50 ml ice cooled absolute DMF. It is stirred for thirty minutes at 0° C. warmed to room temperature. and stirred for a further 60 minutes. Surplus sodium hydride is disposed of by pouring into iced water. The hydrolyzate is extracted three times with ether. The combined organic phases are washed thoroughly with water, dried over MgSO4, filtered, and condensed in a vacuum. The residue is purified by means of column chromatography (silica gel 60; dichloromethane), or by distillation in a vacuum.

3-methoxyphenyl-methyl-sulphide (69)

Educt: 3-mercaptoanisol; methyl iodide colourless oil: b.p.: 57°–58° C. yield: 95% $^1$H-NMR(CDCl$_3$): d=2.47(s;3H,—SCH$_3$); 3.78(s;3H,—OCH$_3$); 6.58–6.97(m;3H,ArH); 7.22(t;$^3$J=8 Hz;1H,ArH).

4-methoxyphenyl acetic acid chloride (70)

Prepared as described above under "Preparation of acid chlorides"

colourless oil: b.p.: 79°–81° C. (0.1 mm) yield: 96% IR(Film): 1800 cm$^{-1}$ (s;C=O)

1-(4-methoxy-2-methylthiophenyl)-2-(4-methoxyphenyl)ethanon (71)

The method of synthesis is analogous to the procedure described above for Friedel-Craft's acylation.

Educts: 3-methoxyphenyl-methyl-sulphide (69) 4-methoxyphenyl acetic acid chloride (70)

SC: silica gel 60; dichloromethane colorless crystals (EtOH): M.P.: 88°–89° C.: yield: 48%

1-(4methoxy-2-methylthiphenyl)-2-(4-methoxyphenyl)ethanol (72)

0.3 g (7.9 mmol) lithium aluminium hydride is placed in 50.0 ml absolute ether and cooled in the ice bath to 0°–5° C. 1-(4-methoxy-2-methylthiophenyl)-2-(4-methoxyphenyl)ethanon (71) (6.9 mml) is dissolved in absolute ether and slowly added dropwise to the lithium aluminium hydride suspension. Following that it is heated for one hour to boiling point. After cooling, it is hydrolysed carefully with water, and acidified with dilute hydrochloric acid, until all the alumuinium hydroxide has gone into solution. It is extracted three times with ether, washed twice with water, dried over MgSO4, filtered and condensed in a water jet vacuum. The product is purified by column chromatography with silica gel 60 (eluction medium dichloromethane/ether (19:1).

colourless needles: M.P.: 69°–70° C. yield: 93%

Preparation of 1-alkyl-1,2-diarylethanols 1.2 g (49.5 mmol) magnesium chips are activated with a small quantity of iodine by warming and washing in nitrogen. Following this, 49.5 mmol alkylhalogenide in 20 ml absolute ether are added dropwise to the activated magnesium chips under nitrogen. The reaction commences on the ether boiling. When all the alkylhalogenide has been added, the mixture is refluxed for one hour. After cooling it is added slowly to 50 g (16.5 mmol) 1-(4-methoxy-2-methylthiophenyl)-2-(4-methoxyphenyl)ethanon (71) in 40 ml absolute ether, and heated for two hours in reflex. The cooled mixture is hydrolysed with water, acidified with dilute hydrochloric acid and extracted three times with ether. The combined organic phases are washed with water, filtered and condensed in a water jet vacuum. The residue is chromatographed with dichloromethane over silica gel 60.

2-(4-methoxy-2-methylthiophenyl)-1-(4-methoxyphenyl)propan-2ol (73)

Educt: 1-(4-methoxy-2-methylthiophenyl)-2-(4-methyoxyphenyl)ethanon (71), methyl iodide yellow oil: yield: 82% IR(Film): 3420 cm$^{-1}$ (m; br; —OH)

2-(4-methoxy-2-methylthiophenyl)-1-(4-methoxyphenyl)-butan-2-ol (74)

Educt: 1-(4-methoxy-2-methylthiophenyl)-2-(4-methoxyphenyl)ethanon (71) ethyl iodide yellow oil: yield: 78% IR(Film): 3560 cm$^{-1}$ (m; br; —OH)

2-(4-methoxy-2-methylthiophenyl)-1-(4-methoxyphenyl)-pentan-2-ol (75)

Educt: 1-(4-methoxy-2-methylthiophenyl)-2-(4-methoxyphenyl)ethanon (71) propyl iodide yellow oil: yield: 94% IR(Film): 3560 cm$^{-1}$ (m; br; —OH)

2-(4-methoxy-2-methylthiophenyl)-1-(4-methoxyphenyl)-3-phenylpropan-2-ol (76)

Educt: 1-(4-methoxy-2-methylthiophenyl)-2-(4-methoxyphenyl)ethan (71) benzyl chloride yellow oil: yield: 44% IR(Film): 3560 cm$^{-1}$ (m; br; —OH)

2-hydroxy-2-(4-methoxy-2-methylthiophenyl)-1-(4-methoxyphenyl)-oct-7-en (77)

In this case absolute tetrahydrofuran is used as the solvent for preparation of the Grignard reagent. 6-bromine-1-hexen and 1-(4-methoxy-2-methylthiophenyl)-2-(4-methoxyphenyl)ethanon (71) are used as educts.

colourless oil: yield: 85% IR(Film): 3560 cm$^{-1}$ (m; br; —OH)

Dehydration of 1-alkyl-1,2-diarylethanols

Alcohol (ca. 5.0 g) is dissolved in 100 ml toluol, mixed with 10.0 g oxalic acid, and heated for 24 hours reflux in a water separator. After cooling, the oxalic acid is filtered off, and washed thoroughly with toluol. The organic phases are washed with water, dried over MgSO4 and filtered. After removal of the solvent in vacuum, it is chromatographed with dichloromethane/petrol ether 40°–60° C. (1:1, by vol) over silica gel 60. Since dehydration may entail two possible ways (with the exception of 72) of losing water, up to four isomers can be formed. However, only two isomers respectively were found, which could not be separated. The ratio of isomers formed lies more than 50% in favour of the 1-alkenes.

1-(4-methoxy-2-methylthiophenyl)-2-(4-methyoxyphenyl)ethen (78)

Educt: 1-(4-methoxy-2-methylthiophenyl)-2-(4-methoxyphenyl)ethanol (72)

colourless crystals: M.P.: 69°–70° C. yield: 79%

2-(4-methoxy-2-methylthiophenyl)-1-(4-methoxyphenyl)propen (79)

Educt: 2-(4-methyoxy-2-methylthiophenyl)-1-(4-methoxyphenyl)propan-2-ol (73)

colourless crystals: M.P.: 55°–58° C. yield: 85%

2-(4-methoxy-2-methylthiophenyl)-1-(4-methoxyphenyl)but-1-en (81)

Educt: 2-(4-methoxy-2-methylthiophenyl)-1-(4-methoxyphenyl)butan-2-ol (74)

colourless oil: yield: 76% $^1$H-NMR(CDCl$_3$): d=0.96-(t;$^3$J=7 Hz;3H,—CH$_2$CH$_3$); 2.40(s; 3H,—SCH3); 2.66 (q; $^3$J=7 Hz; 2H, —CH$_2$CH$_3$); 3.75 (s; 3H, —OCH3); 3.83 (s; 3H, —OCH3); 6.36–7.16 (m; 7H, ArH); 7.31 (d; $^3$J=9 Hz;1H,ArH).

2-(4-methoxy-2-methylthiophenyl)-1-(4-methoxyphenyl)pent-1-en (83)

Educt: 2-(4-methoxy-2-methylthiophenyl)-1-(4-methoxyphenyl)pentan-2-ol (75)

yellow oil: yield: 88% $^1$H-NMR(CDCl$_3$): d=0.86 (t;$^3$J=7 Hz;3H,—CH2CH$_2$CH$_3$) 1.29–1.75 (m; 2H,—CH2CH2CH3); 2.41 (s; 3H,—SCH$_3$); 2.34–2.74 (m; 2H, —CH$_2$CH$_2$CH$_3$); 3.75 (s; 3H, —CH3); 3.83 (s; 3H, —OCH3); 6.37–7.38 (m; 8H, ArH).

2-(4-methoxy-2-methylthiophenyl)-1-(4-methoxyphenyl)-3-phenyl-prop-1-en (85)

Educt: 2-(4-methoxy-2-methylthiophenyl)-1-(4-methoxyphenyl)-3-propan-2-ol (76)

yellow crystals(EtOH): M.P.: 98°–101° C. yield : 82%

2-(4-methoxy-2-methylthiophenyl)-1-(4-methoxyphenyl)octa-1,7-dien (87)

Educt: 2-hydroxy-2-(4-methoxy-2-methylthiophenyl)-1-(4-methyoxyphenyl)oct-7-en(77)

colourless oil: yield: 95% $^1$H-NMR(CDCl$_3$): d=1.22–2.84(m; 8H, —(CH$_2$)$_4$—); 2.40(s; 3H,—SCH3); 3.72 (s; —OCH$_3$); 3.80 (s; 3H, —OCH3); 4.70–5.05 (m; 2H, —CH$_2$CH=CH$_2$); 5.28–6.02 (m; 1H, —CH$_2$CH=CH$_2$); 6.26–7.24(m; 8H, ArH).

2-bromine-4-methoxyphenylsulphonyl chloride (133) and 4-bromine-2methoxyphenylsulphonyl chloride (134)

A solution of 20.0 g (106.9 mmol) 3-bromoanisole in 100 ml absolute dichloromethane is cooled to 0° C. in the ice bath. This is followed by slow (ca 45 minutes) dropwise addition of 25.0 g (214.0 mmol, 14.2 ml) chlorosulphonic acid. Precipitated sulphonic acid derivatives will go into solution later. Should the production of HCl cease, phosphor pentachloride is added in portions until a clear homogeneous solution results, and no increase in HCl production is detected. Thirty minutes stirring in the ice bath follows, then it is poured onto iced water, the phases are separated in the separating funnel, and the aqueous phases are extracted twice with dichloromethane. The combined organic phases are washed with water over MgSO4, filtered and condensed in a vacuum. The residue is purified by column chromatography (silica gel 60; dichloromethane). The synthesis produces two isomers, which are not separated at this stage. Compound 133: 2-bromine-4-methoxyphenylsulphonyl chloride Compound 134: 4-bromine-2-methoxyphenylsulphonyl chloride The formation ratio depends heavily on the conditions of the reaction, in which the formation of compound 133 is dominant. The following points relate to the mixture of isomers.

colourless crystals (etOH): M.P.: 79°–80° C.; yield: 97% C$_7$H$_6$O$_3$SBrCl (285.5) Ber.: C 29.44 H 2.12 Gef.: C 29.43 H 1.92

2-bromine-4-methoxyphenylmecaptan (135) and 4-bromine-2-methoxyphenylmercaptan (136)

A mixture of 1.12 g (36.2 mmol) red phosphor, 4.5 ml glacial acetic acid and 53.0 mg (0.2 mmol) iodine are gently heated to boiling point in a three-necked flask with reflux condenser. At a steadily maintained temperature, 13.3 mmol of a mixture of (133) and (134) are added in portions in such a way as to prevent the escape of the iodine vapour which is formed. Following this, the mixture is heated for two hours reflux. It is allowed to cool slightly, 0.8 ml water are added and refluxed again for one hour. After cooling it is diluted with 50 ml water and extracted three times with dichloromethane. The combined organic phases are washed free of acidity with water, dried over MgSO4, filtered and condensed in a vacuum.

The residue is chromatographed with petroleum ether 40°–60° C./acetic ether (9:1, by vol.) over silica gel 60. Compounds 135 and 136 are not separable.

colourless oil: b.p.: 73°–76° C.; yield: 71% IR (Film): 2560 cm$^{-1}$ (w: —SH)

2-bromine-4-methoxyphenylthioacetate (137)

By-product of synthesising 135 and 136. Yields vary between 0 and 40%.

yellow oil: IR (Film): 1710 cm$^{-1}$ (s;C=O)

2-bromine-4-methoxyphenyl-methyl-sulphide (138) and 4-bromine-2-methoxyphenyl-methyl-sulphide (139)

The method of synthesis is analogous to the procedure for methylising thiophenols. The mixture of compounds 135 and 136 is used as source material. The resulting thioether mixture is separated by column chromatography (silica gel 60) using petroleum ether 40°–60° C./acetic ether (9:1 by vol.). Yields depend on the formation ratio of compounds 133 and 134.

1. Fraction: 4-bromine-2-methoxyphenyl-methyl-sulphide (139) colourless crystals (EtOH): M.P.: 54°–55° C.; yield: 20–54%

2. Fraction: 2-bromine-4-methoxyphenyl-methyl-sulphide (138)

colourless oil: b.p.: 81°–86° C. (0.1 mm); yield: 40–70% 1H-NMR (CDCl$_3$) δ=2.44 (s;3H, —SCH$_3$); 3.79 (s;3H, —OCH$_3$); 6.86 (dd; $^3$J=9 Hz; 4J=3 Hz; 1H, ArH); 7.16 (d, $^4$J=3 Hz, 1H, ArH); 7.20 (d;$^3$J=9 Hz; 1H,ArH).

Preparation of alkyl-4-methoxybenzyl-ketones

Apparatus must be kept constantly under nitrogen!

A solution of 0.3 mol alkylmagnesium halogenide made from 0.3 mol (7.3 g) magnesium chips and 0.3 mol alkyl halogenide in 200 ml absolute ether is added in portions to 0.15 mol (32.8 g) anhydrous cadmium chloride while being stirred constantly and powerfully (KPG stirrer). It is heated to boiling point for thirty minutes, then the reflux cooler is replaced with a distillation bridge, and around 150 ml of ether are distilled off. The residue is mixed with 250 ml absolute benzol. While being stirred vigorously and at room temperature, a solution of 0.2 mol (36.9 g) 4-methoxphenyl acetic acid chloride (70) in 70 ml absolute benzol is added dropwise. Following this the mixture is heated for 1 hour in reflux. After cooling it is hydrolized carefully with 2N hydrochloric acid. The organic phase is separated off in the separating funnel, washed twice with saturated sodium hydrogen carbonate solution and water and dried over MgSO4. The drying agent is removed by filtration, the solvent is drawn off in a vacuum, and the residue distilled in an oil pump vacuum.

1-(4-methoxyphenyl)butan-2-on (140)

Educts: 4-methoxyphenyl acetic acid chloride (70); ethyl iodide colourless oil: b.p.: 72°–76° C. (0.1 mm); yield: 59% IR (Film): 1720 cm$^{-1}$ (s;C=O)

1-(4-methoxyphenyl)pentan-2-on (141)

Educts: 4-methoxyphenyl acetic acid chloride (70); propyl iodide light yellow oil: b.p.: 84°–88° C. (0.1 mm); yield: 51% IR (Film): 1720 cm$^{-1}$ (s;C=O)

Preparation of 1-alkyl-1,2-diarylethanols

While being washed in nitrogen, 0.5 g (21.4 mmol) magnesium chips are activated by warming with some iodine (formation of iodine vapour). Following this a solution of 5.0 g (21.4 mmol) 2-bromine-4-methoxyphenyl-methyl-sulphide (138) in 30 ml absolute tetrahydrofuran (THF) is slowly added dropwise to the activated magnesium chips. The reaction starts as the solvent boils and the reaction solution simultaneously discolours. The Grignard reagent is heated in reflux for 1 hour. After cooling, a solution of 24.0 mmol of a corresponding ketone in 20 ml absolute THF is added dropwise, it is heated again for 2 hours in reflux, and after cooling the solution is hydrolized with 2N hydrochloric acid. The hydrolyzate is extracted three times with ether, washed with saturated sodium hydrogen carbonate solution and water, and dried over MgSO4. The drying agent is removed by filtration, the solvent drawn off in a vacuum. and the residue chromatographed with petroleum ether 40°–60° C./acetic ether (3:1 by vol.) over silica gel 60. Occasionally water splitting may lead to formation of stilbenes. which may be isolated as a subsequent product, crystallising from ethanol.

2-(5-methoxy-2-methylthiophenyl)-1-(4-methoxyphenyl)-propan-2-ol (142)

Educts: 2-bromine-4-methoxyphenyl-methyl-sulphide(138) 4-methoxyphenyl acetone yellow oil: yield: 27% IR (Film): 3440 cm$^{-1}$ (s, br; —OH)

2-(5-methoxy-2-methylthiophenyl)-1-(4-methoxyphenyl)-propen (145)

By-product of preparation of 142.

colourless crystals (EtOH): M.P.: 112°–113° C.: yield: 13%

2-(5-methoxy-2-methylthiophenyl)-1-(4-methoxyphenyl)-butan-2-ol (143)

Educts: 2-bromine-4-methoxyphenyl-methyl-sulphide(138) 1-(4-methoxyphenyl)butan-2-on (140)

yellow oil: yield: 27% IR (Film): 3550 cm$^{-1}$ (m, br; —OH)

2-(5-methoxy-2-methylthiophenyl)-1-(4-methoxyphenyl)but-1-en (147)

By-product of preparation of 143.

Colourless crystals (MeOH): M.P.: 108°–109° C.; yield: 15%

2-(5-methoxy-2-methylthiophenyl)-1-(4-methoxyphenyl)-pentan-2-ol (144)

Educts: 2-bromine-4-methoxyphenyl-methyl-sulphide(138) 1-(4-methoxyphenyl)-pentan-2-on (141)

yellow oil: yield: 46% IR (Film): 3540 cm$^{-1}$ (m, br: —OH)

Dehydration of 1-alkyl-1,2-diarylethanols

The method of synthesis is analogous to the procedure for dehydrating alcohols (see above: compound (78)). The isomers formed cannot be separated.

2-(5-methoxy-2-methylthiophenyl)-1-(4-methoxyphenyl)-propen (145)

Educt: 2-(5-methoxy-2-methylthiophenyl)-1-(4-methoxyphenyl)propan-2-ol (142) For analytical data see the preceding section "Preparation of 1-alkyl-1,2-diarylethanols"

2-(5-methoxy-2-methylthiophenyl)-1-4-methoxyphenyl)-but-1-en (147)

Educt: 2-(5-methoxy-2-methylthiophenyl)-1-4-methoxyphenyl)butan-2-ol (143) For analytical data see above.

2-(5-methoxy-2-methylthiophenyl)-1-(4-methoxyphenyl)-pent-1-en (149)

Educt: 2-(5-methoxy-2-methylthiophenyl)-1-4-methoxyphenyl)pentan-2-ol (144)

yellow oil: yield: 83% $^1$H-NMR (CDCl$_3$): d=0.87 (t; $^3$J=7Hz; 3H,—CH$_2$CH$_2$CH$_3$); 1.38–1.82 (m; 2H,—CH$_2$CH$_2$CH$_3$); 2.39 (s; 3H,—SCH$_3$); 2.52–2.83 (m; 2H,—CH$_2$CH$_2$CH$_3$); 3.77 (s; 3H, OCH$_3$); 3.80 (s; 3H,—OCH$_3$); 6.35–7.40 (m; 8H, ArH).

EXAMPLES

Ether separation and cyclizing

In an apparatus which has been rinsed in nitrogen a solution of 4.0 mmol 1.2-diarylethanone in 8.0 ml absolute dichloromethane is cooled in an ice bath to 0° C., and slowly (ca. 10 minutes) mixed with a solution of 4.0 g (16.0 mmol: 1.5 ml) boron tribromide in 5.0 ml absolute dichloromethane. It is stirred for 30 minutes at 5°–10° C. taken from the ice bath and stirred overnight at room temperature. Following this, it is ice-cooled and sufficient 10% sodium hydrogen carbonate solution added until the strong reaction ceases, then it is mixed with 20 ml acetic ether and stirred for 15 minutes at room temperature. The phases are separated in a separating funnel. The aqueous phase is extracted three times with water, the combined organic phases washed with water and dried over MgSO4. After the drying agent has been filtered off, the solvent is drawn off in a vacuum. The residue is chromatographed with dichloromethane/acetic ether (9:1) over silica gel 60. The products are as a rule crystallised from hot dichloromethane.

1.) 5-hydroxy-2-(4-hydroxyphenyl)benzo[b]furan (60a)
Educt: 2-(2.5-dimethoxyphenyl)-1-(4-methoxyphenyl)ethanon (51a)
colourless crystals: M.P.: 243°–245° C.; yield: 34%

2.) 6-hydroxy-2-(4-hydroxyphenyl)benzo[b]furan (60b)
Educt: 2-(2,4-dimethoxyphenyl)-1-(4-methoxyphenyl)ethanon (51b)
beige crystals: M.P.: 239°–241° C.; yield: 23%

3.) 5-hydroxy-2-(4-hydroxyphenyl)methylbenzo[b]furan (61a)
Educt: 2-(2,5-dimethoxyphenyl)-1-(4-methoxyphenyl)propanon (53a)
yellowish crystals: M.P.: 154°–155° C.; yield: 53%

4.) 6-hydroxy-2-(4-hydroxyphenyl)-3-methylbenzo[b]furan (61b)
Educt: 2-(2,4-dimethoxyphenyl)-1-(4-methoxyphenyl)propanon (53a)
colourless crystals: M.P.: 191°–192° C.; yield: 21%

5.) 3-ethyl-5-hydroxy-2-(4-hydroxyphenyl)benzo[b]furan (62a)
Educt: 2-(2,5-dimethoxyphenyl)-1-(4-methoxyphenyl)butanon (54a)
colourless crystals: M.P.: 163°–164° C.; yield: 30%

6.) 3-ethyl-6-hydroxy-2-(4-hydroxyphenyl)benzo[b]furan (62b)
Educt: 2-(2.4-dimethoxyphenyl)-1-(4-methoxyphenyl)butanon (54b)
beige crystals: M.P.: 125°–127° C.; yield: 19%

7.) 5-hydroxy-2-(4-hydroxyphenyl)-3-propylbenzo[b]furan (63a)
Educt: 2-(2,5-dimethoxyphenyl)-1-(4-methoxyphenyl)pentanon (55a)
colourless crystals: M.P.: 127°–128° C.; yield: 44%

8.) 6-hydroxy-2-(4-hydroxyphenyl)-3-propylbenzo[b]furan (60b)
Educt: 2-(2.4-dimethoxyphenyl)-1-(4-methoxyphenyl)pentanon (55b)
colourless crystals: M.P.: 151°–152° C.; yield: 23%

9.) 3-butyl-5-hydroxy-2-(4-hydroxyphenyl)benzo[b]furan (64a)
Educt: 2-(2.5-dimethoxyphenyl)-1-(4-methoxyphenyl)hexanon (56a)
colourless crystals: M.P.: 124°–125° C.; yield: 40%

10.) 3-butyl-6-hydroxy-2-(4-hydroxyphenyl)benzo[b]furan (64b)
Educt: 2-(2,4-dimethoxyphenyl)-1-(4-methoxyphenyl)hexanon (56b)
colourless needles: M.P.: 169°–170° C.; yield: 29%

11.) 3-(6 bromine hexyl)-5-hydroxy-2-(4-hydroxyphenyl)benzo[b]furan (67a)
Educt: 8-bromine-2-(2,5-dimethoxyphenyl)-1-(4-methoxyphenyl)octanon (59a)
colourless crystals: M.P.: 146°–148° C.: on dissolution yield: 40%

12.) 3-(6-bromine hexyl)-6-hydroxy-2-(4-hydroxyphenyl)benzo[b]furan (67a)
Educt: 8-bromine-2-(2,4-dimethoxyphenyl)-1-(4-methoxyphenyl)octanon (59a)
colourless crystals: M.P.: 89°–91° C.; yield: 43%

Procedure for piperidine substitution 0.2 mmol of the 3-(6-bromine hexyl)-benzo[b]furans 67a and 67b, each dissolved in 50 ml piperidine, are heated for four hours in reflux in a 100 ml round flask. After cooling, surplus piperidine is removed in a vacuum. The residue is chromatographed with dichloromethane/ethanol (19:1) over neutral aluminium oxide, activity grade 2.

13.) 5-hydroxy-2-(4-hydroxyphenyl)-3-(6-N-piperidylhexyl)benzo[b]furan (68a)
Educt: 3-(6-bromine hexyl)-5-hydroxy-2-(4-hydroxyphenyl)benzo[b]furan (67a)
light beige crystals: M.P.: 190°–191° C.; yield: 36%
6-hydroxy-2-(4-hydroxyphenyl)-3-(6-N-piperidylhexyl)benzo[b]furan (68b)
Educt: 3-(6-bromine hexyl)-6-hydroxy-2-(4-hydroxyphenyl)benzo[b]furan (67)
light beige crystals: M.P.: 115° C. on decomposition yield: 36%

Cyclization into benzo[b]thiophens* *Ruwet, A. and Renson, M., Bull. Soc. Chim. Belg., 1970, 79, 593–599

14.0 mmol of a 1,2-diarylalkene are dissolved in 20 ml absolute chloroform, and cooled to 0° C. in an ice bath. Following this, 14.5 mmol (1.96 g; 1.17 ml) sulphuryl chloride are slowly added dropwise to 10 ml absolute chloroform. This is stirred for one hour in the ice bath and the solvent drawn off in a vacuum, during which the temperature of the water bath must not rise above 40° C. The oily residue is added to 20 ml absolute pyridine and heated for one hour in reflux. After the mixture has cooled, it is poured onto iced water, acidified with concentrated hydrochloric acid and extracted three times with dichloromethane. The combined organic phases are washed twice with water, dried over MgSO4, filtered and condensed in a vacuum. The residue is chromatographed with dichloromethane/petroleum ether 40°–60° C. (1:1 by vol.). The product crystallises as rule from ethanol. Two isomers are isolated, since the 1,2-diarylalkenes are used in the form of an isomer mixture.

14.) 6-methoxy-2-(4-methoxyphenyl)benzo[b]thiophen (89b)
Educt: 1-(4-methoxy-2-methylthiophenyl)-2-(4-methoxyphenyl)ethan (78)
colourless crystals (EtOH): M.P.: 191°–193° C.; yield: 82% Lit.: 193°–194° C.

15.) 6-methoxy-2-(4-methoxyphenyl)-3-methylbenzo[b]thiophen (90b)
Educt: 2-(4-methoxy-2-methylthiophenyl)-1-(4-methoxyphenyl)propen (79)
colourless needles (EtOH); M.P.: 98°–99° C.; yield: 41%

16.) 3-ethyl-6-methoxy-2-(4-methoxyphenyl)benzo[b]

thiophen (92b)

Educt: 2-(4-methoxy-2-methylthiophenyl)-1-(4-methoxyphenyl)but-1-en (81)

colourless crystals: M.P.: 90°–91° C.; yield: 38%

17.) 6-methoxy-2-(4-methoxyphenyl)-3-propylbenzo[b]thiophen (94b)

Educt: 2-(4-methoxy-2-methylthiophenyl)-1-(4-methoxyphenyl)pent-1-en (83)

colourless needles (EtOH): M.P.: 96°–97° C.; yield: 41%

18.) 3-(hex-5-en-1yl)-6-methoxy-2-(4-methoxyphenyl)benzo[b]thiophen (98b)

Educt: 2-(4-methoxy-2-methylthiophenyl)-1-(4-methoxyphenyl)octa-1,7-dien (87)

light yellow oil; yield: 53%

Ether separation

Apparatus must be washed in nitrogen! 4.0 mmol of the alkoxy compound which is to be separated is dissolved in 6.5 mol absolute dichloromethane and cooled in the ice bath. For each alkoxy group, 1.05 g (4.2 mmol) or 0.4 ml boron tribromide (99.99%) are dissolved in 2 ml absolute dichloromethane and slowly (ca. 10 minutes) added dropwise under nitrogen. It is stirred for ca. 30 minutes at 3°–5° C., taken from the ice bath, and stirred for 2 hours at room temperature. It is ice-cooled again, and sodium hydrogen carbonate solution added until the powerful hydrolysis reaction ceases. It is mixed with acetic ether, stirred for ca. 30 minutes at room temperature, and the phases separated in a separating funnel. The aqueous phases are extracted twice more with acetic ether. The combined organic phases are washed twice with water, dried over MgSO4, filtered, and the solvent drawn off in a vacuum (30°–40° C. bath temperature). The raw product is purified by column chromatography (silica gel 60). A mixture of dichloromethane/acetic ether (9:1 by vol.) is used as the moving phase. The purified product crystallises as a rule from dichloromethane with the addition of a small amount of acetic ether.

19.) 6-hydroxy-2-(4-hydroxyphenyl)benzo[b]thiophen (101b)

Educt: 6-methoxy-2-(4-methoxyphenyl)benzo[b]thiophen (89b)

colourless crystals: M.P.: 252°–254° C.; yield: 63%

20.) 6-hydroxy-2-(4-hydroxyphenyl)-3-methylbenzo[b]thiophen (102b)

Educt: 6-methoxy-2-(4-methoxyphenyl)-3-methylbenzo[b]thiophen (90b)

beige crystals; M.P.: 223°–225° C.; yield: 36%

21.) 3-ethyl-6-hydroxy-2-(4-hydroxyphenyl)benzo[b]thiophen (104b)

·Educt: 3-ethyl-6-methoxy-2-(4-methoxyphenyl)benzo[b]thiophen (92b)

colourless crystals: M.P.: 160°–161° C.; yield: 31%

22.) 6-hydroxy-2-(4-hydroxyphenyl)-3-propylbenzo[b]thiophen (106b)

Educt: 6-methoxy-2-(4-methoxyphenyl)-3propylbenzo[b]thiophen (94b)

colourless crystals: M.P.: 115°–117° C.; yield: 43%

Hydroboration with 9-boron bi-cyclo(3.3.1)nonan (9-BBN)* *Zablocki, J. A. et al., J. Med. Chem., 1987, 30, 829–838

17.0 g of a solution of 0.5M 9-BBN (8.4 mmol) in absolute THF is added dropwise to a solution of 1.4 mmol alkene in 5.0 ml absolute tetrahydrofuran (THF) at 0° C. under a nitrogen atmosphere. After stirring for forty minutes at 60° C. it is cooled in the ice bath to 0° C., mixed with 3.0 ml water and stirred for a further 5 minutes. Following this, 3.0 ml 3N-sodium hydroxide solution are added, it is ice-cooled and stirred for a further 5 minutes, and 3.0 ml 30% hydrogen peroxide solution slowly added dropwise. The mixture is stirred for 30 minutes, following which 10 ml saturated sodium hydrogen carbonate solution is added. The mixture is extracted three times with acetic ether, washed thoroughly with water, and dried over MgSO4. The drying agent is removed by filtration, the solvent drawn off in a vacuum and the residue chromatographed with dichloromethane/acetic ether (4:1 by vol.) over silica gel 60.

23.) 3-(6-hydroxyhexyl)-6-methoxy-2-(4-methoxyphenyl)benzo[b]thiophen (110b)

Educt: 3-(hex-5-en-1-yl)-6-methoxy-2-(4-methoxyphenyl)benzo[b]thiophen (98b)

colourless oil: yield: 73% IR (Film) 3360 cm$^{-1}$ (s; br: —OH)

Methanesulphonylation of alcohols*

2.0 mmol of a primary alcohol are dissolved in 20 ml absolute THF under nitrogen and added to 20.0 mmol triethylamine (2.0 g, 2.8 ml). Following this, a solution of 10.0 mmol methanesulphonyl chloride (1.4 g, 1.0 ml) in 5.0 ml absolute THF is slowly added dropwise. A white precipitate forms immediately. After stirring for thirty minutes, 30 ml saturated sodium hydrogen carbonate solution are added, and the mixture is extracted three times with acetic ether. The combined organic phases are washed with saturated sodium chloride solution and water, dried over MgSO4, filtered and condensed in a vacuum. The residue is purified by column chromatography (silica gel 60) with dichloromethane as the moving phase. Crystalline products are recrystallised from ethanol.

24.) 3-(6-methanesulphonyloxyhexyl)-6-methoxy-2-(4-methoxyphenyl)benzo[b]thiophen (113b)

Educt: 3-(6-hydroxyphenyl)-6-methoxy-2-(4-methoxyphenyl)benzo[b]thiophen (110b)

colourless oil; yield: 76% IR (Film) 1340 cm$^{-1}$; 1170 cm$^{-1}$ (s, —SO$_2$O—)

Substitution with piperidine 5.0 mmol piperidine (0.43 g, 0.5 ml) is added to a solution of 1.0 mmol methanesulphonate in 4.0 ml acetonitrile/triethylamine (1:1 by vol.) and stirred overnight at room temperature. Surplus piperidine is drown off in a vacuum together with the solvent. The residue is taken up in acetic ether, washed twice with water and dried over MgSO4. The drying agent is removed by filtration, the solvent drawn off in a vacuum, and the residue chromatographed with acetic ether/triethylamine (30:1 by vol.) over silica gel 60.

25.) 6-methoxy-2-(4-methoxyphenyl)-3-(6-N-piperidinylhexyl) benzo[b]thiophen (110b)

Educts: 3-(6-methanesulphonyloxyhexyl)-6-methoxy-2-(4-methoxyphenyl)benzo[b]thiophen (113b); piperidine yellow oil: yield: 60% 1H-NMR (CDCl$_3$): d=1.10–1.80 (m; 14H, —CH$_2$)$_7$); 2.10–2.45 (m: 6H, —N(CH$_2$)$_3$; 2.80 (t; $^3$J=7 Hz; 2H, =CCH$_2$CH$_2$); 3.84 (s; 3H, —OCH$_3$); 3.86 (s; 3H, —OCH$_3$); 7.01 (dd; $^3$J=9 Hz; $^4$J=2 Hz; 1H, ArH); 7.31 (d; $^4$J=2 Hz; 1H, ArH); 7.61 (d; $^3$J=9 Hz; 1H,ArH); 6.97,7.44 (AA'BB'; $^3$J=9 Hz; 4H, ArH).

Ether separation

The method of ether separation is analogous to the general procedure preceding compound 101b. Twenty times the amount of absolute dichloromethane is used as the solvent.

The raw products are chromatographed with an acetic ether/ triethylamine/ethanol mixture over silica gel 60. The products crystallise from dichloromethane/acetic ether with the addition of hexane.

26.) 6-hydroxy-2-(4-hydroxyphenyl)-3-(6-N-piperidinylhexyl)benzo[b]thiophen (119b)

Educt: 6-methoxy-2-(4-methoxyphenyl)-3-(6-N-piperidinylhexyl)benzo[b]thiophen (116b); Flow agent for the column chromatography; acetic ether/NEt$_3$/EtOH (10/10/1, V/V/V)

beige crystals; M.P.: 115° C. on decomposition yield: 46%

Cyclization of the 1.2-diarylalkenes* *Ruwet, A. and Renson, M., Bull.Soc.Chim.Belg., 1970, 79, 593–599

The method of synthesis follows the general procedure described under "Cytclization into benzo[b]-thiophen". Two isomers are isolated. since the 1,2-diarylalkenes used are in the form of an isomer mixture. Further benzo[b]thiophen derivatives are produced as by-products, and these are additionally chlorinated on the C4 atom.

27.) 5-methoxy-2-(4-methoxyphenyl)-3-methylbenzo[b]thiophen (90a)

Educt: 2-(5-methoxy-2methylthiophenyl)-1-(4-methoxyphenyl)propen (145);

colourless needles (EtOH); M.P.; 106°–107° C. yield: 41%

28.) 3-ethyl-5Methoxy-2-(4-methoxyphenyl)benzo[b]thiophen (92a)

Educt: 2-(5-methoxy-2-methylthiophenyl)-1-(4-methoxyphenyl)but-1-en (147);

Yellow crystals (EtOH); M.P.: 116°–117° C. yield: 48%

29.) 5-methoxy-2-(4-methoxyphenyl)-3-propylbenxo[b]thiophen (94a)

Educt: 2-(5-methoxy-2-methylthiophenyl)-1-(4-methoxyphenyl)pent-1-en (149);

colourless crystals (EtOH); M.P.: 76°–77° C. yield: 47%

Ether separation

The method of ether separation is analogous to the general procedure. The raw products are purified by column chromatography (silica gel 60) with dichloromethane/acetic ether (9:1 by vol.) as the moving phase. The products crystallise from hot dichloromethane.

30.) 5-hydroxy-2-(4-hydroxypheny)-3-methyibenxo[b]thiophen (102a)

Educt: 5-methoxy-2-(4-methoxyphenyl)-3-methylbenzo[b]thiophen (90a)

colourless crystals; M.P.: 204°–205° C. yield: 71%

31.) 3-ethyl-5-hydroxy-2-(4-hydroxyphenyl)benzo[b]thiophen (104a)

Educt: 3-ethyl-5-methoxy-2-(4-methoxypphenyl)benzo[b]thiophen (92a)

colourless crystals: M.P.: 173°–174° C. yield 78%

32.) 5-hydroxy-2-(4-hydroxyphenyl)-3-propylbenzo[b]thiophen (106a)

Educt: 5-methoxy-2-(4-methoxyphenyl)-3-propylbenzo[b]thiophen (94a)

colourless crystals; M.P.; 152°–153° C. yield 81%

Introduction of a side chain into 2-phenylbenzo[b]thiophens a) 3-(6-bromohexanoyl)-6-methoxy-2-(4-methoxyphenyl)benzo[b]thiophen 1.40 g (5.13 mmol) 6methoxy-2-(4-methoxyphenyl)benzo[b]thiophen[1]is added to a solution of 1.09 g (5.13 mmol) 6-bromohexanoic acid chloride in 50 ml 1.2-dichloroethane. Following this 0.80 g (6.15 mmol) AlCl$_3$are added in three portions while stirring at room temperature. After stirring for one hour. After washing with saturated NaCl solution and drying (MgSO4), the solvent is drawn off. and the residue purified by column chromatography (SiO$_2$; CH$_2$Cl$_2$/petroleum ether 3:1).

A yellow oil is produced with a yield of 55%

[1]Jones, C. D., Jevmikov, M. G., Pike, A. J., Peters, M. K., Black, L. J., Thompson, A. R., Falcone, J. F., Clemens, J. A.; H.Med.Chem. 1984, 27, 1057–1066 b) 3-(6-broxohexyl)-6-methoxy-2-(4-methoxyphenyl)benzo[b]thiophen 46.0 mg (1.21 mmol) LiAlH$_4$ are placed in 1 ml dry ether under nitrogen. After cooling in the ice bath. 161.6 mg (1.21 mmol) AlCl$_3$ in 1 mi dry ether are added dropwise. After 1 minute. the ice bath is removed and 542.0 mg (1.21 mmol) 3-(6-bromohexyl)-6-methoxy-2-(4-methoxyphenyl)benzo[b]thiophen in 2 mi dry ether are added dropwise while boiling gently. After 30 minutes the mixture is ice-cooled and 2 mi 6N H$_2$SO$_4$ are added consecutively. The mixture is extracted with ether. After washing with water and drying, the ether is drawn off and the product recrystallised from n-hexane.

Colourless crystals; M.P.: 93°–95° C. yield: 80%

I claim:

1. A 2-Phenylbenzo[b]furan or -thiophene of formula I

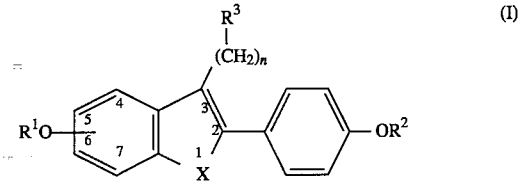

wherein $R^1$ and $R^2$ each independently are hydrogen; $C_{1-10}$-alkyl; benzyl; $C(O)R^4$, wherein $R^4$ is $C_{1-10}$-alkyl or -alkoxy, or a phenyl radical; or a carbamoyl group —$C(O)NR^5R^6$, wherein $R^5$ and $R^6$ each independently are hydrogen or $C_{1-10}$-alkyl; and when $R^3$ is an amino group —$NR^7R^8$, wherein $R^7$ and $R^8$, each independently, are hydrogen or $C_{1-10}$-alkyl, or $R^7$ and $R^8$ together are an alkylene group—$(CH_2)_m$—, or —$(CH_2)_2O(CH_2)_2$—, wherein m is 2, 3, 4, 5 or 6;

X is O or S; and n is an integer from 4 to 12 when X is S, or n is an integer from 5 to 12 when X is O; or when $R^3$ is hydrogen, X is S, and n is 2–12.

2. A compound of claim 1, which is 5-hydroxy-2-(4-hydroxyphenyl)-3-(6-N-piperidylhexyl)-benzo[b]furan, 6-hydroxy-2-(4-hydroxphenyl)-3-(6-N-piperidylhexyl)-benzo[b]furan, 3-ethyl-6-hydroxy-2-(4-hydroxyphenyl)benzo[b]thiophen, 6-hydroxy-2-(4-hydroxyphenyl)-3-propylbenzo[b]thiophen, or 6-hydroxy-2-(4-hydroxyphenyl)-3-(6-N-piperidinylhexyl)-benzo[b]thiophen.

3. A pharmaceutical preparations comprising an effective amount of a compound of claim 1 and an inert pharmaceutically acceptable carrier.

4. A pharmaceutical preparations comprising an effective amount of a compound of claim 2 and an inert pharmaceutically acceptable carrier.

5. A method of inducing an antiestrogenic effect in a patient in need of such treatment, comprising administering an effective amount of a compound of claim 1.

6. A method of inducing an antiestrogenic effect in a patient in need of such treatment, comprising administering an effective amount of a compound of claim 2.

7. A method of treating an estrogen-dependent disease or condition in a patient in need of such treatment, comprising administering an effective amount of a compound of claim 1.

8. A method of treating an estrogen-dependent disease or condition in a patient in need of such treatment comprising administering an effective amount of a compound of claim 2.

9. A method of claim 7, wherein said disease or condition is prostate hyperplasia, mammary carcinoma, endometrial carcinoma, anovulatory infertility or melanoma.

10. A method of claim 8, wherein said disease or condition is prostate hyperplasia, mammary carcinoma, endometrial carcinoma, anovulatory infertility or melanoma.

* * * * *